United States Patent
Burkot et al.

(10) Patent No.: US 10,576,235 B2
(45) Date of Patent: Mar. 3, 2020

(54) MANAGEMENT OF A THERAPEUTIC OXYGEN DELIVERY SYSTEM

(71) Applicant: Tokitae LLC, Bellevue, WA (US)

(72) Inventors: Stephen Thomas Graves Burkot, Bellevue, WA (US); Ryan Calderon, Seattle, WA (US); Mark K. Kuiper, Seattle, WA (US); Daniel Howard Lieberman, Bellevue, WA (US); Chin Hei Ng, Newcastle, WA (US)

(73) Assignee: TOKITAE LLC, Bellevue, WA (US)

( * ) Notice: Subject to any disclaimer, the term of this patent is extended or adjusted under 35 U.S.C. 154(b) by 274 days.

(21) Appl. No.: 15/598,510

(22) Filed: May 18, 2017

(65) Prior Publication Data

US 2018/0333554 A1    Nov. 22, 2018

(51) Int. Cl.
*A61M 16/10* (2006.01)
*G16H 40/60* (2018.01)
(Continued)

(52) U.S. Cl.
CPC .......... *A61M 16/101* (2014.02); *G16H 20/40* (2018.01); *G16H 40/60* (2018.01);
(Continued)

(58) Field of Classification Search
CPC ............ A61M 16/101; A61M 2202/00; A61M 2202/02; A61M 16/00; A61M 16/0057;
(Continued)

(56) References Cited

U.S. PATENT DOCUMENTS 6,551,384 B1    4/2003  Ackley et al.
6,764,534 B2    7/2004  McCombs et al.
(Continued)

FOREIGN PATENT DOCUMENTS

JP    4404583    3/2005

OTHER PUBLICATIONS

PCT International Search Report; International App. No. PCT/US2018/032243; dated Sep. 21, 2018; pp. 1-3.

*Primary Examiner* — Jason E Flick
(74) *Attorney, Agent, or Firm* — Daniel J. Honz; Advent, LLP

(57) ABSTRACT

Described embodiments include a therapeutic oxygen supply apparatus. The apparatus includes at least two components, including an intake manifold component configured to receive concentrated oxygen, a compressor component configured to compress concentrated oxygen, an oxygen tank component configured to store concentrated oxygen, a patient manifold component configured to supply concentrated oxygen, or a control structure component configured to route a flow of concentrated oxygen. A sensor circuit acquires data indicative of a respective operational state of the at least two components. A rule-based engine selects a next operational state of a component in response to (i) the acquired data indicative of the respective operational states of the at least two components and (ii) a rule database having at least one rule responsive to an objective providing a therapeutic flow of oxygen to the patient. A configuration manager circuit generates a control signal implementing the selected next operational state.

16 Claims, 8 Drawing Sheets

(51) Int. Cl.
*G16H 20/40* (2018.01)
*A61M 16/00* (2006.01)

(52) U.S. Cl.
CPC . *A61M 16/0063* (2014.02); *A61M 2016/1025* (2013.01); *A61M 2202/0208* (2013.01); *A61M 2205/16* (2013.01); *A61M 2205/3334* (2013.01); *A61M 2205/50* (2013.01); *A61M 2205/84* (2013.01)

(58) Field of Classification Search
CPC .............. A61M 16/10; A61M 16/1005; A61M 2016/102; A61M 2205/3331; A61M 2205/33; A61M 2205/00; A61M 2202/0208; A61M 16/0063; A61M 2016/1025; A61M 2202/0007; A61M 2205/3334; A61M 2205/50; A61M 2205/84; A61M 16/0051; A61M 2205/16; G16H 20/40; G16H 40/60; G16H 10/00; G61H 20/00; G61H 40/00; A62B 9/006
See application file for complete search history.

(56) References Cited

U.S. PATENT DOCUMENTS

| | | | |
|---|---|---|---|
| 7,121,276 B2 | 10/2006 | Jagger et al. | |
| 7,350,521 B2 | 4/2008 | Whitley et al. | |
| 7,510,601 B2 | 3/2009 | Whitley et al. | |
| 7,857,894 B2 | 12/2010 | Taylor et al. | |
| 7,976,617 B2 | 7/2011 | Kao | |
| 7,998,256 B2 | 8/2011 | Kao | |
| 8,123,497 B2 | 2/2012 | Richey, II et al. | |
| 8,568,519 B2 | 10/2013 | Taylor et al. | |
| 8,702,840 B1 | 4/2014 | Friedman et al. | |
| 9,138,557 B2 | 9/2015 | Wilkinson et al. | |
| 2006/0174877 A1 | 8/2006 | Jagger et al. | |
| 2006/0260711 A1 | 11/2006 | Fry et al. | |
| 2009/0107500 A1 | 4/2009 | Edwards | |
| 2009/0212962 A1 | 8/2009 | Chekal et al. | |
| 2010/0116270 A1 | 5/2010 | Edwards et al. | |
| 2011/0247620 A1 | 10/2011 | Armstrong et al. | |
| 2014/0261426 A1 | 9/2014 | Ahmad et al. | |
| 2014/0345609 A1* | 11/2014 | Whitcher | C01B 13/0259 128/202.26 |
| 2015/0107585 A1 | 4/2015 | Allum | |
| 2015/0273174 A1 | 10/2015 | Hart et al. | |
| 2016/0317966 A1 | 11/2016 | Kao | |

* cited by examiner

505 A non-transitory storage medium.

510 One or more instructions for acquiring data indicative of a respective operational state of each of at least two components of a therapeutic oxygen supply apparatus.

520 One or more instructions comprising a rule-based engine configured to select a next operational state for a component of the at least two components of the therapeutic oxygen supply apparatus in response to (i) the data indicative of the respective operational state of each of the at least two components and (ii) a rule database having at least one rule responsive to an objective of providing a therapeutic flow of oxygen to a patient.

530 One or more instructions for implementing the selected next operational state in the component.

MANAGEMENT OF A THERAPEUTIC OXYGEN DELIVERY SYSTEM

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

There is a need for a therapeutic oxygen delivery system in hospitals and medical facilities operating in regions where electrical power is subject to interruptions. There is a need in these hospitals and medical facilities for a solution to a technical problem of a dependable therapeutic oxygen delivery system capable of both delivering therapeutic concentrated oxygen to patients and storing concentrated oxygen that will be quickly available for therapeutic delivery to patients if a power interruption occurs.

For example, and without limitation, an embodiment of the subject matter described herein includes a therapeutic oxygen supply apparatus. The apparatus includes at least two components. The at least two components include an intake manifold component configured to receive a concentrated oxygen, a compressor component configured to compress the concentrated oxygen, an oxygen tank component configured to store the concentrated oxygen, a patient manifold component configured to supply the concentrated oxygen to a patient, or an oxygen-flow control structure component configured to route a flow of the concentrated oxygen between the intake manifold and the patient manifold. The apparatus includes a sensor circuit configured to acquire data indicative of a respective operational state of the at least two components. The apparatus includes a rule-based engine configured to select a next operational state of a component of the at least two components of the therapeutic oxygen supply apparatus. The selection is responsive to (i) the acquired data indicative of the respective operational states of the at least two components and (ii) a rule database having at least one rule responsive to an objective of providing a therapeutic flow of oxygen to the patient. The apparatus includes a configuration manager circuit configured to generate a control signal implementing the selected next operational state in the component of the at least two component. In an embodiment, the apparatus includes an oxygen concentrator component.

For example, and without limitation, an embodiment of the subject matter described herein includes a system. The system includes a sensor circuit configured to acquire data indicative of a respective operational state of at least two components of a therapeutic oxygen supply apparatus. The system includes a rule-based engine configured to select a next operational state of a component of the at least two components of the therapeutic oxygen supply apparatus. The selection is responsive to (i) the acquired data indicative of the respective operational state of the at least two components and (ii) a rule database having at least one rule responsive to an objective of providing a therapeutic flow of oxygen to a patient. The system includes a configuration manager circuit configured to generate a control signal implementing the selected next operational state in the component of the at least two components.

For example, and without limitation, an embodiment of the subject matter described herein includes a computationally implemented method. The method includes acquiring data indicative of a respective operational state of at least two components of a therapeutic oxygen supply apparatus. The method includes selecting a next operational state for a component of the at least two components of the therapeutic oxygen supply apparatus. The selection is responsive to (i) the data indicative of the respective operational state of the at least two components and (ii) a rule database having at least one rule responsive to an objective of providing a therapeutic flow of oxygen to a patient. The method includes implementing the selected next operational state in the component.

For example, and without limitation, an embodiment of the subject matter described herein includes a system. The system includes means for sensing data indicative of a respective operational state of at least two components of a therapeutic oxygen supply apparatus. The system includes means for selecting a next operational state for a component of the at least two components of the therapeutic oxygen supply apparatus. The selection is responsive to (i) the data indicative of the respective operational state of the at least two components and (ii) a rule database having at least one rule responsive to an objective of providing a therapeutic flow of oxygen to a patient. The system includes means for implementing the selected next operational state in the component.

In an embodiment, the system includes means for concentrating oxygen from ambient air. In an embodiment, the system includes means for controlling a flow of the concentrated oxygen between the intake manifold and the patient manifold.

For example, and without limitation, an embodiment of the subject matter described herein includes an article of manufacture. The article of manufacture includes a non-transitory computer-readable medium. The non-transitory computer-readable medium bears one or more instructions for acquiring data indicative of a respective operational state of at least two components of a therapeutic oxygen supply apparatus. The non-transitory computer-readable medium bears one or more instructions comprising a rule-based engine configured to select a next operational state for a component of the at least two components of the therapeutic oxygen supply apparatus. The selection is responsive to (i) the data indicative of the respective operational state of the at least two components and (ii) a rule database having at least one rule responsive to an objective of providing a therapeutic flow of oxygen to a patient. The non-transitory computer-readable medium bears one or more instructions for implementing the selected next operational state in the component.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6 illustrates an example article of manufacture in which embodiments may be implemented;

DETAILED DESCRIPTION

Figure 1:
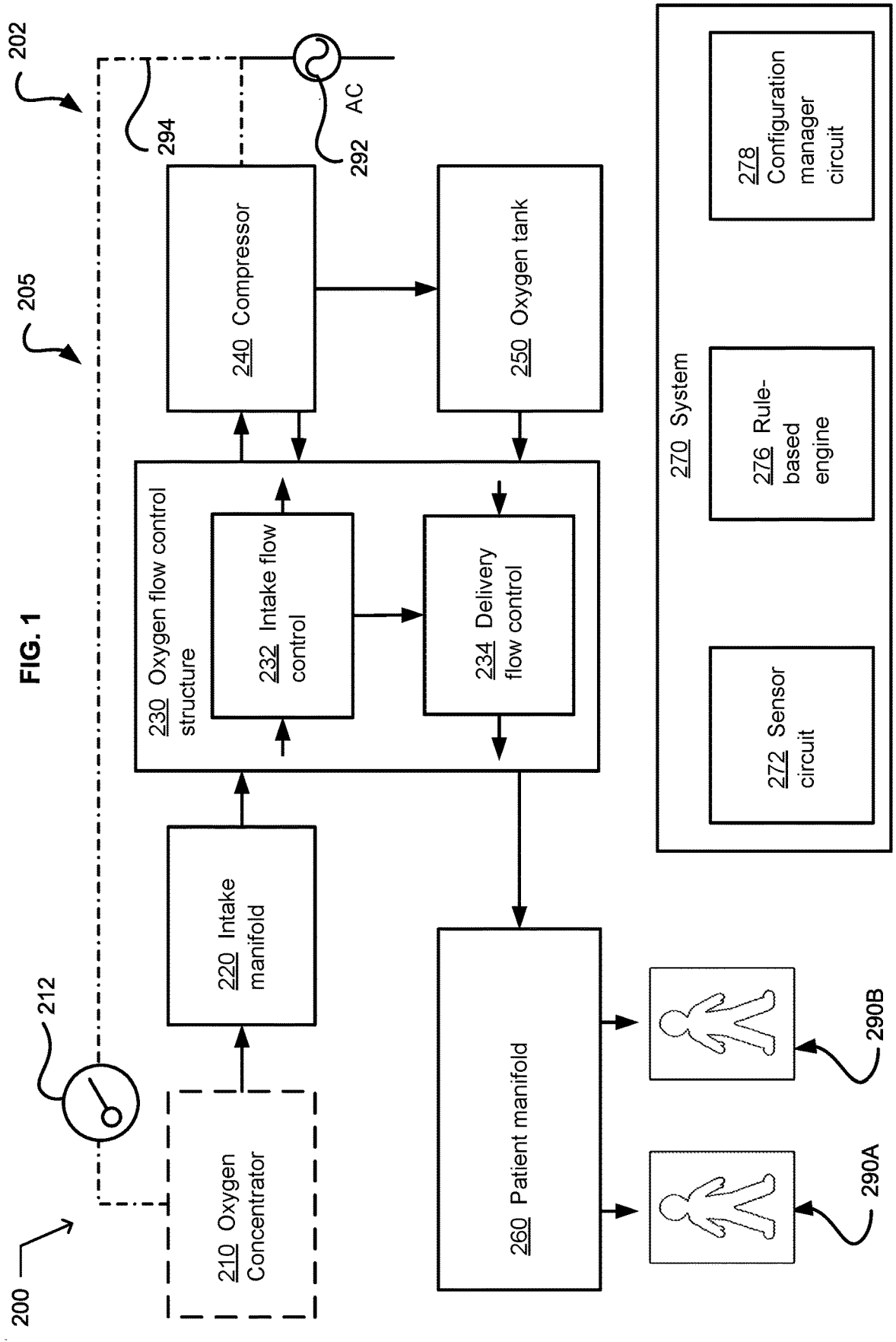
FIG. 1 illustrates an example environment in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various implementations by which processes and/or systems and/or other technologies described herein can be effected (e.g., hardware, software, and/or firmware), and that the preferred implementation will vary with the context in which the processes and/or systems and/or other technologies are deployed. For example, if an implementer determines that speed and accuracy are paramount, the implementer may opt for a mainly hardware and/or firmware implementation; alternatively, if flexibility is paramount, the implementer may opt for a mainly software implementation; or, yet again alternatively, the implementer may opt for some combination of hardware, software, and/or firmware. Hence, there are several possible implementations by which the processes and/or devices and/or other technologies described herein may be effected, none of which is inherently superior to the other in that any implementation to be utilized is a choice dependent upon the context in which the implementation will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to implement an operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, module, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "circuitry" or "electrical circuitry." Consequently, as used herein "circuitry" and "electrical circuitry" both include, but are not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

FIG. 1 illustrates an example environment 200 in which embodiments may be implemented. The environment includes a therapeutic oxygen supply apparatus 202 and a patient, illustrated by a patient 290A and a patient 290B. The therapeutic oxygen supply apparatus includes at least two components 205. A component of the at least two components may include an intake manifold component 220 configured to receive a concentrated oxygen. For example, the concentrated oxygen may be supplied by an oxygen concentrator 210. The at least two components may include a compressor component 240 configured to compress the concentrated oxygen. A component of the at least two components may include an oxygen tank component 250 configured to store the concentrated oxygen. A component of the at least two components may include a patient manifold component 260 configured to supply the concentrated oxygen to a patient on demand. A component of the at least two components may include an oxygen-flow control structure component 230 configured to route a flow of the concentrated oxygen between the intake manifold and the patient manifold.

Figure 2:
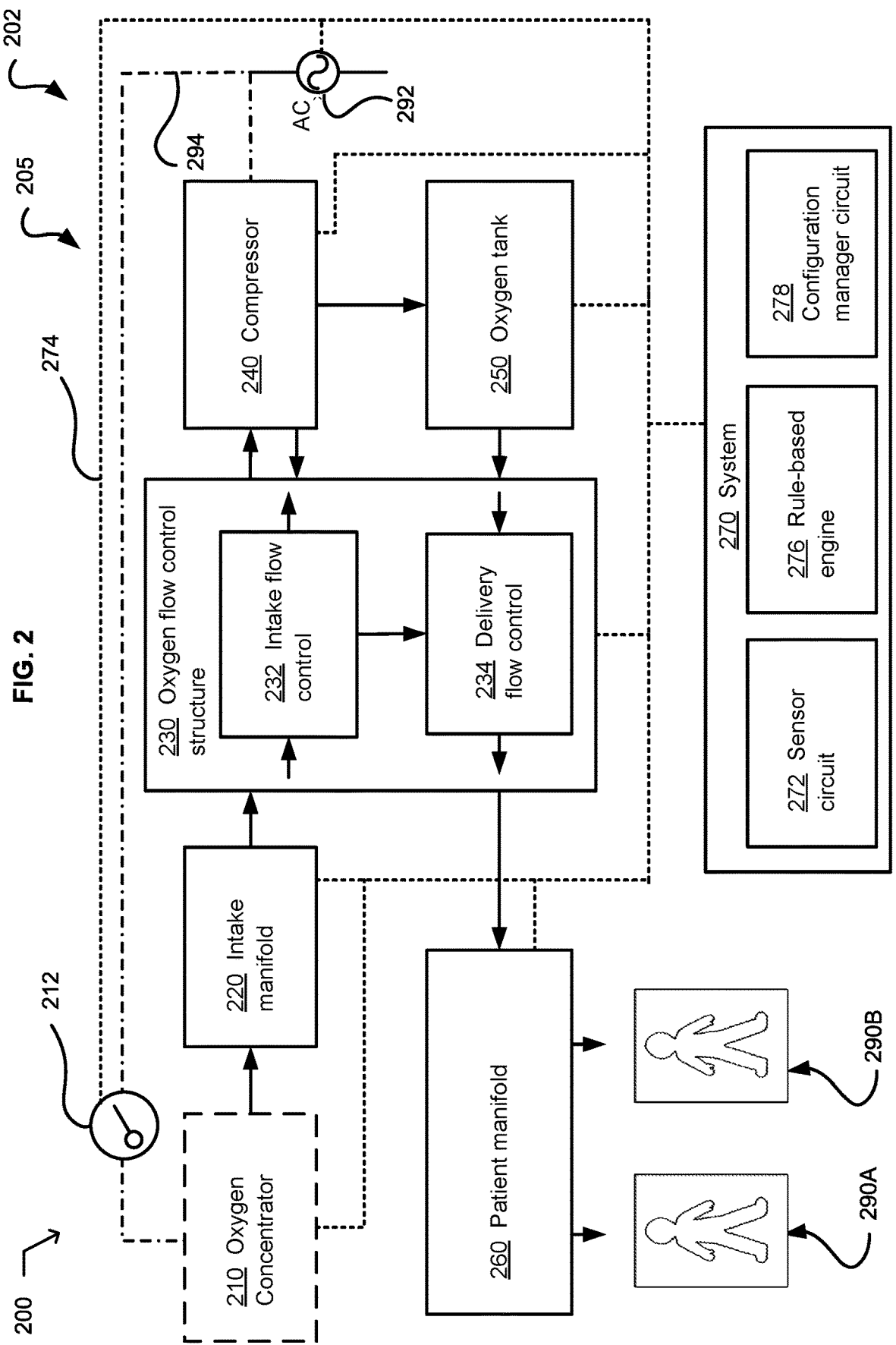
FIG. 2 schematically illustrates an embodiment of the sensor circuit that includes a respective sensor coupled to the at least two components.

The therapeutic oxygen supply apparatus 202 includes a system 270. The system includes a sensor circuit 272 configured to acquire data indicative of a respective operational state of the at least two components 205. FIG. 2 schematically illustrates an embodiment of the sensor circuit that includes a respective sensor 274 coupled to the at least two components. The system includes a rule-based engine 276 configured to select a next operational state of a component of the at least two components of the therapeutic oxygen supply apparatus 202. The selection is responsive to (i) the acquired data indicative of the respective operational states of the at least two components and (ii) a rule database having at least one rule responsive to an objective of providing a therapeutic flow of oxygen to the patient. In an embodiment, the rule-based engine is configured to iteratively select a next operational state of a component of the at least two components of the therapeutic oxygen supply apparatus. The system includes a configuration manager circuit 278 configured to generate a control signal implementing the selected next operational state in the component of the at least two components.

In an embodiment of the therapeutic oxygen supply apparatus 202, the at least two components 205 of the therapeutic oxygen system further include a power supply component 292 configured to supply to electrical power 294 to the at least two components. In an embodiment, the power supply component is configured to supply electrical power to an oxygen concentrator 210 coupled with the intake manifold 220. In an embodiment, the power supply component may be a gas power source, such as bottled natural gas or a natural gas pipeline. In an embodiment, the electrical power supply component is connected to the oxygen concentrator component via a switch or connector 212. In an embodiment, the sensor circuit 272 is further configured to acquire data indicative of a quality of the concentrated oxygen in the therapeutic oxygen supply apparatus. For example, the quality may be measured by a purity, concentration, smell, particulate, or toxicity. For example, the quality may be measured for a purity above a threshold, such as greater than 85% purity. In an embodiment, the sensor circuit is further configured to acquire data indicative of a quality of the concentrated oxygen present in the intake manifold component, oxygen tank component, or the patient manifold component. In an embodiment, the at least two components of the therapeutic oxygen system further include a low oxygen concentration alarm component. For example, the low oxygen concentration alarm component may be configured to activate an alarm if the oxygen concentration is less than 85% purity.

Figure 3:
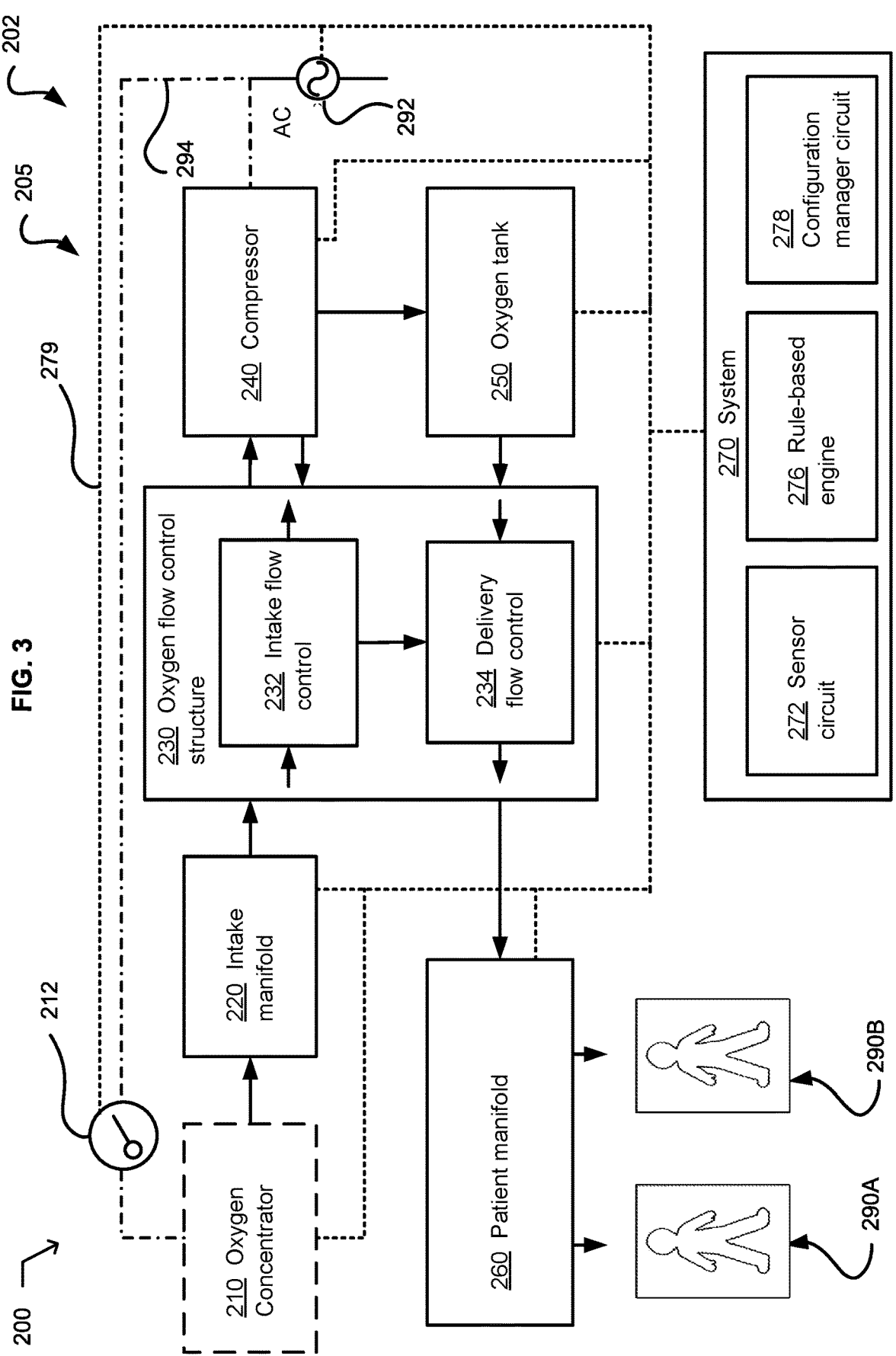
FIG. 3 schematically illustrates the operational-state controller coupled to the at least two components and configured to control an operational state of at least one of the at least two components.

In an embodiment of the therapeutic oxygen supply apparatus 202, the configuration manager circuit 278 includes an operational state controller configured to control an operational state of at least one of the at least two components 205. FIG. 3 schematically illustrates the operational state controller 279 coupled to the at least two components and configured to control an operational state of at least one of the at least two components. In an embodiment, the oxygen-flow control structure component 230 is configured to route a flow of the concentrated oxygen from the intake manifold 220 to the compressor component 240, the oxygen tank component 250, and the patient manifold 260 in response to one or more control signals. In an embodiment, the oxygen-flow control structure component is configured to route a flow of the concentrated oxygen from the intake manifold to the patient manifold in response to one or more control signals. In an embodiment, the oxygen-flow control structure component is configured in response to one or more control signals from the configuration manager circuit to route a flow of the concentrated oxygen from (i) the intake manifold to the compressor component, the oxygen tank component, and the patient manifold; or (ii) from the intake manifold to the oxygen-flow control structure tank component and the patient manifold. In an embodiment, the therapeutic oxygen supply apparatus further includes an oxygen concentrator component 210.

FIG. 1 illustrates an embodiment of the system 270. The system includes the sensor circuit 272 configured to acquire data indicative of a respective operational state of at least two components 205 of the therapeutic oxygen supply apparatus 202. The system includes the rule-based engine 276 configured to select a next operational state of a component of the at least two components of the therapeutic oxygen supply apparatus. The selection is responsive to (i) the acquired data indicative of the respective operational state of the at least two components and (ii) a rule database having at least one rule responsive to an objective of providing a therapeutic flow of oxygen to a patient. In an embodiment, the rule-based engine is configured to iteratively select a next operational state of a component of the at least two components of the therapeutic oxygen supply apparatus. The system includes the configuration manager circuit 278 configured to generate a control signal implementing the selected next operational state in a component of the at least two components.

In an embodiment, the sensor circuit 272 includes a sensor responsive to an operational state of a component of the at least two components 205. FIG. 2 schematically illustrates an embodiment of the sensor circuit that includes a respective sensor device 274 coupled to the at least two components. In an embodiment, the sensor circuit includes a first sensor device responsive to an operational state of a first component of the at least two components and a second sensor device responsive to an operational state of a second component of the at least two components. In an embodiment, the sensor 274 may include a separate sensing device respectively associated with the at least two components. For example, a sensor device associated with the intake manifold component 220 may include an oxygen flow sensor or a pressure sensor device. For example, a sensor device associated with the oxygen tank 250 may include a pressure sensor, or a load or weight sensor device. For example, a sensor device associated with the patient manifold component 260 may include an oxygen flow sensor or a pressure sensor device. For example, a sensor device associated with the switch or connector 212 may include a voltage sensor device. In an embodiment, the sensor circuit is further configured to collect, compute, or infer data indicative of an operational state of a component of the at least two components of the therapeutic oxygen supply apparatus. In an embodiment, the data indicative of an operational state includes data indicative of a quality of the concentrated oxygen in the therapeutic oxygen supply apparatus 202. In an embodiment, the data indicative of a quality of the concentrated oxygen includes data indicative of a concentrated oxygen quality at an intake manifold component 220 of the therapeutic oxygen supply apparatus. In an embodiment, the data indicative of a quality of the concentrated oxygen includes data indicative of a concentrated oxygen quality at a compressor component 240 of the therapeutic oxygen system. In an embodiment, the data indicative of a quality of the concentrated oxygen includes data indicative of a concentrated oxygen quality at an oxygen tank component 250 of the therapeutic oxygen supply apparatus. In an embodiment, the data indicative of a quality of the concentrated oxygen includes data indicative of a concentrated oxygen quality at a patient manifold component 260 of the therapeutic oxygen supply apparatus. In an embodiment, the data indicative of a quality of the concentrated oxygen includes data indicative of a concentrated oxygen quality received by the oxygen-flow control structure component 230 of therapeutic oxygen system.

In an embodiment, the sensor circuit 272 is configured to acquire data indicative of a fill state of the oxygen tank component 250 of the therapeutic oxygen system 202. For example, a fill state may include empty, partially filled, filling, or full state. In an embodiment, the sensor circuit is configured to acquire data indicative of an activity state of the compressor component 240 of the therapeutic oxygen system. For example, an activity state may include an on, off, speed, powered, or no power state. In an embodiment, the sensor circuit is configured to acquire data indicative of a state of a power source 292 supplying electrical power to at least one component of the therapeutic oxygen system. For example, a state of the power source may include an on, off, or predicted to go off status.

For example, in an embodiment, the rule database of the rule-based engine 276 may include a rule that if the patient 290A is coupled to the patient manifold component 260; then run the oxygen concentrator component 210, run the compressor component 240, and set the oxygen flow control structure component 230 to route the concentrated oxygen to the patient manifold component. For example, in an embodiment, the rule database may include a rule that if no patient is coupled to the patient manifold component and if the oxygen tank component is not in a full state; then run the oxygen concentrator component, run the compressor component, and set the oxygen flow control structure component to route the concentrated oxygen flow to the oxygen tank component 250. In an embodiment, the rule database includes a rule database having (a) a first priority (or first level) rule responsive to an objective of providing a therapeutic flow of oxygen to a patient; and (b) a second priority (or second level) rule responsive to an objective of filling the oxygen tank component of the therapeutic oxygen system. For example, in an embodiment, the rule database may include a rule that if the patient is coupled to the patient manifold component and if the oxygen tank component in not in a full state; then run the oxygen concentrator component, run the compressor component, and set the oxygen flow control structure component to divide the flow of concentrated oxygen flow between the oxygen tank component and the patient manifold component. In an embodiment, the rule database includes a rule database having (a) a first priority rule responsive to an objective of providing a therapeutic flow of oxygen to a patient; (b) a second priority rule responsive to an objective of filling an oxygen tank component of the therapeutic oxygen system; and (c) a third priority rule responsive to minimizing electrical power consumption by the therapeutic oxygen supply apparatus. In an embodiment, the rule-based engine is further configured to resolve the select the next operational state as a constraint satisfaction problem.

In an embodiment, the configuration manager circuit 278 is configured to control an operational state of at least one of the at least two components 205 of the therapeutic oxygen supply apparatus 202.

In an embodiment, the at least two components 205 include an intake manifold component 220 configured to receive a concentrated oxygen, a compressor component 240 configured to compress the concentrated oxygen, an oxygen tank component 250 configured to store the concentrated oxygen, a patient manifold component 260 configured to supply the concentrated oxygen to a patient, or an oxygen-flow control structure component 230 configured to route a flow of the concentrated oxygen between the intake manifold and the patient manifold. In an embodiment, the at least two components include an oxygen-flow control structure component 230 having an intake flow director 232 and a delivery flow director 234. In an embodiment, the intake flow director is configured to direct in response to a control signal a flow of oxygen received from the intake manifold component to the compressor component or to the delivery flow director. In an embodiment, the intake flow director is configured to direct in response to a control signal a flow of oxygen received from the intake flow director or the oxygen tank component to the patient manifold component. In an embodiment, the at least two components include the oxygen concentrator component 210. In an embodiment, the therapeutic oxygen supply apparatus 202 is configured to receive concentrated oxygen produced from ambient air, store the concentrated oxygen, and deliver the concentrated oxygen to a patient on demand.

Figure 4:
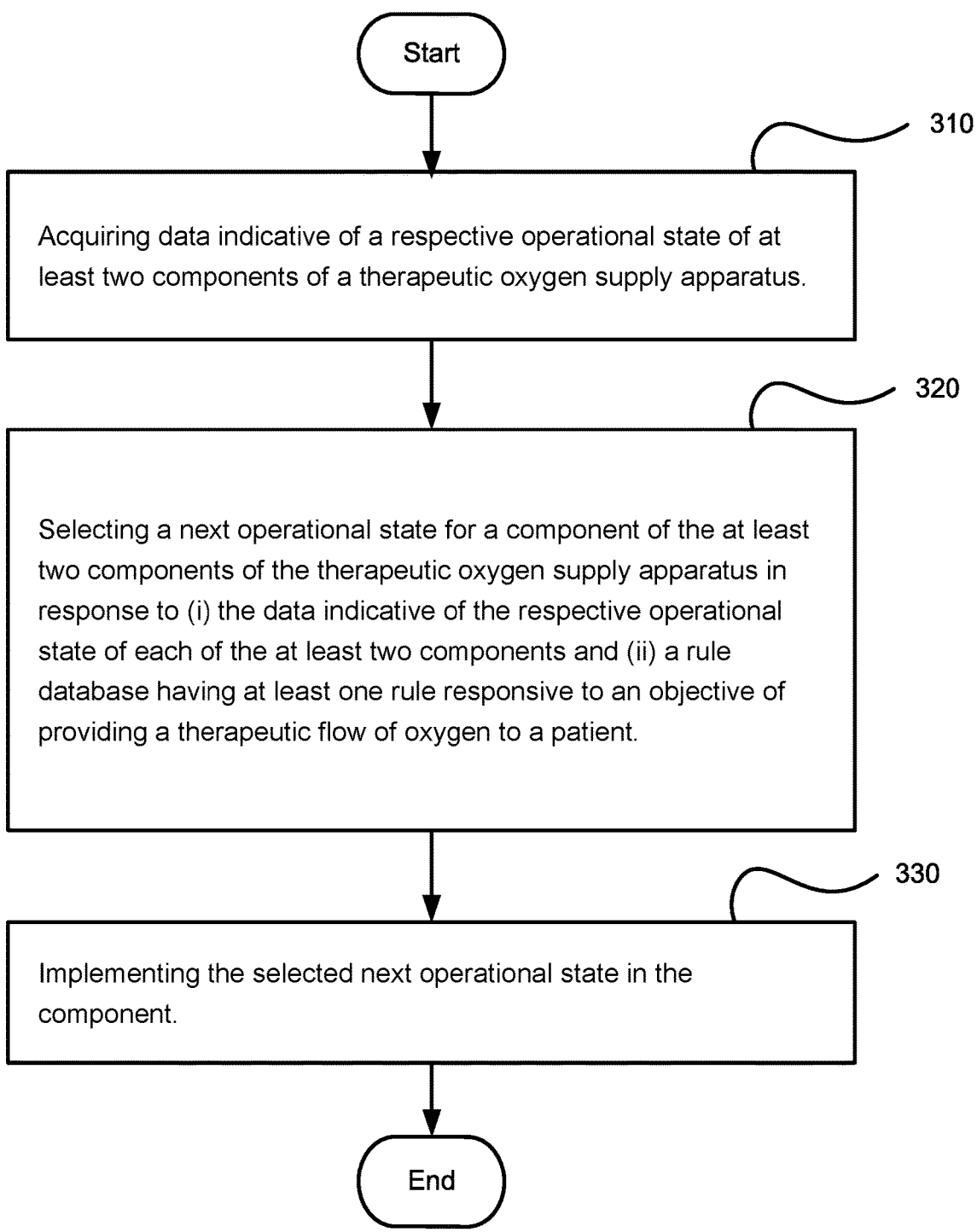
FIG. 4 illustrates an example computationally implemented operational flow in which embodiments may be implemented.

FIG. 4 illustrates an example computationally implemented operational flow 300 in which embodiments may be implemented. In an embodiment, the computationally implemented operational flow may be implemented in a thin computing device. An example of a thin computing device 20 is described below in conjunction with FIG. 7 below. In an embodiment, the computationally implemented operational flow may be implemented in a general purpose computing device. An example of a general purpose computing device 110 is described below in conjunction with FIG. 8 below. After a start operation, the operational flow includes sensing operation 310. The sensing operation includes acquiring data indicative of a respective operational state of at least two components of a therapeutic oxygen supply apparatus. In an embodiment, the sensing operation may be implemented using the sensor circuit 272 of the system 270 described in conjunction with FIG. 1. An oxygen supply configuration operation 320 includes selecting a next operational state for a component of the at least two components of the therapeutic oxygen supply apparatus. The selecting is performed in response to (i) the data indicative of the respective operational state of the at least two components and (ii) a rule database having at least one rule responsive to an objective of providing a therapeutic flow of oxygen to a patient. In an embodiment, oxygen supply configuration operation may be implemented using the rule-based engine 276 described in conjunction with FIG. 1. A reconfiguration operation 330 includes implementing the selected next operational state in the component. In an embodiment, the reconfiguration operation may be implemented using the configuration manager circuit 278 described in conjunction with FIG. 1. The operational flow includes an end operation.

In an embodiment of the oxygen supply configuration operation 320, the rule database includes a rule database having (a) at least one first priority rule responsive to an objective of providing a therapeutic flow of oxygen to a patient; and (b) at least one second priority rule responsive to an objective of filling an oxygen tank component of the therapeutic oxygen system. In an embodiment of the oxygen supply configuration operation, the rule database includes a rule database having (a) at least one first priority rule responsive to an objective of providing a therapeutic flow of oxygen to a patient; (b) at least one second priority rule responsive to an objective of filling an oxygen tank component of the therapeutic oxygen system; and (c) at least one third priority rule response to minimizing electrical power consumption by the therapeutic oxygen supply apparatus.

Figure 5:
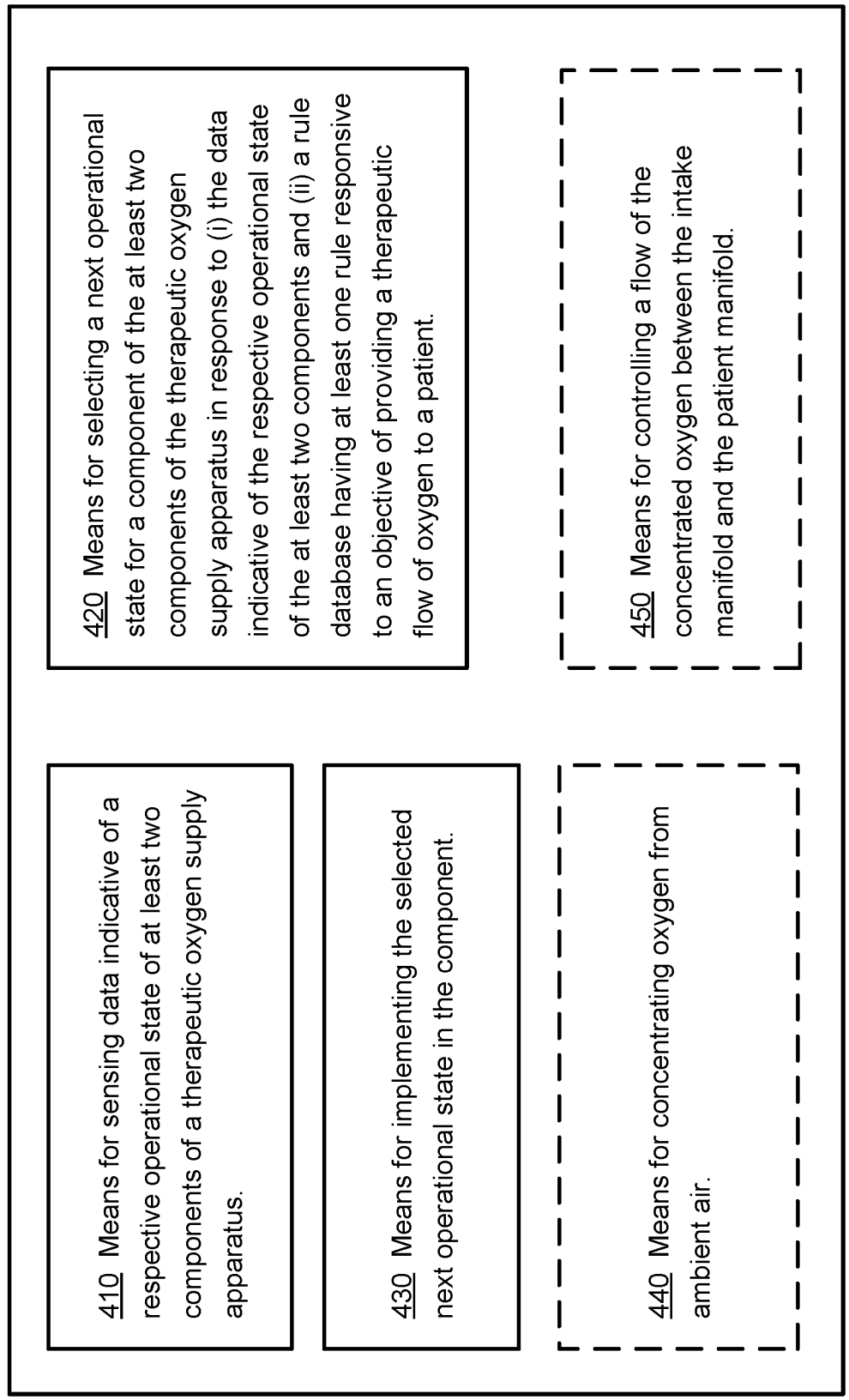
FIG. 5 illustrates an example system in which embodiments may be implemented.

FIG. 5 illustrates an example system 400 in which embodiments may be implemented. The system includes means 410 for sensing data indicative of a respective operational state of at least two components of a therapeutic oxygen supply apparatus. The system includes means 420 for selecting a next operational state for a component of the at least two components of the therapeutic oxygen supply apparatus in response to (i) the data indicative of the respective operational state of the at least two components and (ii) a rule database having at least one rule responsive to an objective of providing a therapeutic flow of oxygen to a patient. The system includes means 430 for implementing the selected next operational state in the component.

In an embodiment, the system includes means 440 for concentrating oxygen from ambient air. In an embodiment, the system includes means 450 for controlling a flow of the concentrated oxygen between the intake manifold and the patient manifold.

FIG. 6 illustrates an example article of manufacture 500 in which embodiments may be implemented. The article of manufacture includes a non-transitory storage medium 505 bearing instructions. The instructions 510 include one or more instructions for acquiring data indicative of a respective operational state of at least two components of a therapeutic oxygen supply apparatus. The instructions 520 include one or more instructions comprising a rule-based engine configured to select a next operational state for a component of the at least two components of the therapeutic oxygen supply apparatus. The selection is responsive to (i) the data indicative of the respective operational state of the at least two components and (ii) a rule database having at least one rule responsive to an objective of providing a therapeutic flow of oxygen to a patient. The instructions 530 include one or more instructions for implementing the selected next operational state in the component.

Figure 7:
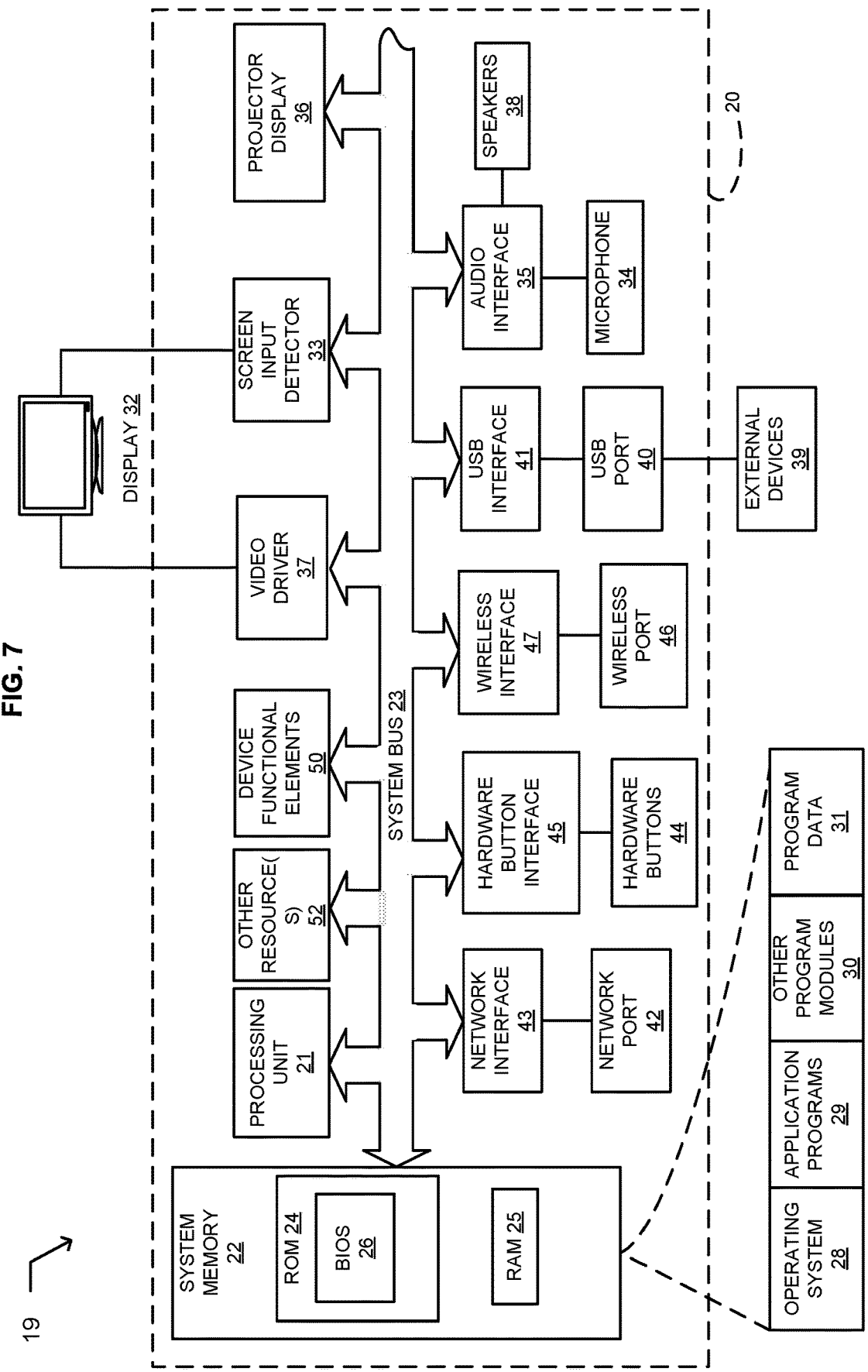
FIG. 7 is generally directed toward a thin computing environment having a thin computing device.
Figure 8:
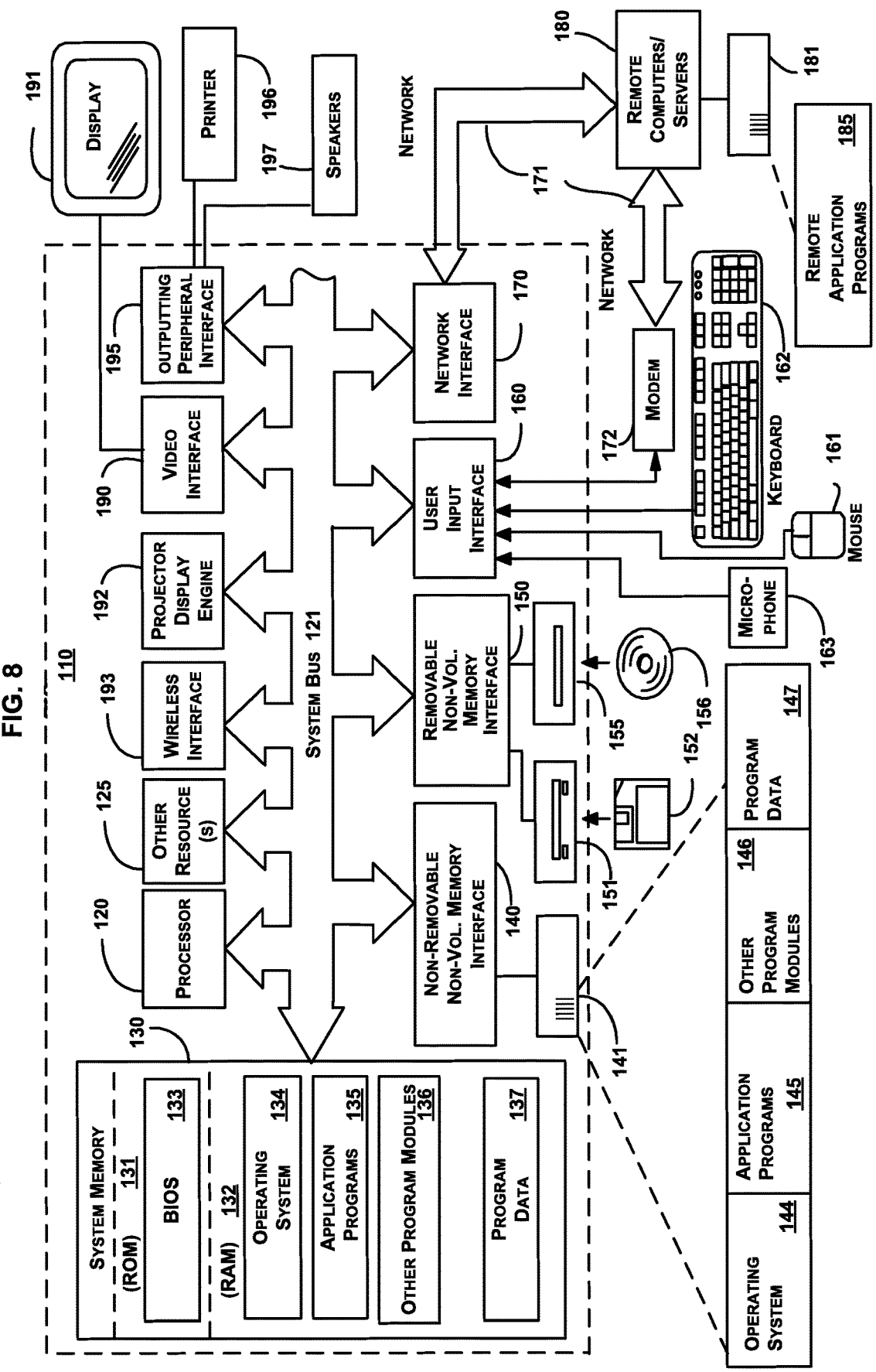
FIG. 8 is generally directed toward a general purpose computing environment having general purpose computing device.

FIGS. 7 and 8 provide respective general descriptions of several environments in which implementations may be implemented. FIG. 7 is generally directed toward a thin computing environment 19 having a thin computing device 20, and FIG. 8 is generally directed toward a general purpose computing environment 100 having general purpose computing device 110. However, as prices of computer components drop and as capacity and speeds increase, there is not always a bright line between a thin computing device and a general purpose computing device. Further, there is a continuous stream of new ideas and applications for environments benefited by use of computing power. As a result, nothing should be construed to limit disclosed subject matter herein to a specific computing environment unless limited by express language.

FIG. 7 and the following discussion are intended to provide a brief, general description of a thin computing environment 19 in which embodiments may be implemented. FIG. 7 illustrates an example system that includes a thin computing device 20, which may be included or embedded in an electronic device that also includes a device functional element 50. For example, the electronic device may include any item having electrical or electronic components playing a role in a functionality of the item, such as for example, a refrigerator, a car, a digital image acquisition device, a camera, a cable modem, a printer an ultrasound device, an x-ray machine, a non-invasive imaging device, or an airplane. For example, the electronic device may include any item that interfaces with or controls a functional element of the item. In another example, the thin computing device may be included in an implantable medical apparatus or device. In a further example, the thin computing device may be operable to communicate with an implantable or implanted medical apparatus. For example, a thin computing device may include a computing device having limited resources or limited processing capability, such as a limited resource computing device, a wireless communication device, a mobile wireless communication device, a smart phone, an electronic pen, a handheld electronic writing device, a scanner, a cell phone, or a tablet device. For example, a thin computing device may include a thin client device or a mobile thin client device, such as a smart phone, tablet, notebook, or desktop hardware configured to function in a virtualized environment.

The thin computing device 20 includes a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system (BIOS) 26, containing the basic routines that help to transfer information between sub-components within the thin computing device 20, such as during start-up, is stored in the ROM 24. A number of program modules may be stored in the ROM 24 or RAM 25, including an operating system 28, one or more application programs 29, other program modules 30 and program data 31.

A user may enter commands and information into the computing device 20 through one or more input interfaces. An input interface may include a touch-sensitive screen or display surface, or one or more switches or buttons with suitable input detection circuitry. A touch-sensitive screen or display surface is illustrated as a touch-sensitive display 32 and screen input detector 33. One or more switches or buttons are illustrated as hardware buttons 44 connected to the system via a hardware button interface 45. The output circuitry of the touch-sensitive display 32 is connected to the system bus 23 via a video driver 37. Other input devices may include a microphone 34 connected through a suitable audio interface 35, or a physical hardware keyboard (not shown). Output devices may include the display 32, or a projector display 36.

In addition to the display 32, the computing device 20 may include other peripheral output devices, such as at least one speaker 38. Other external input or output devices 39, such as a joystick, game pad, satellite dish, scanner, or the like may be connected to the processing unit 21 through a USB port 40 and USB port interface 41, to the system bus 23. Alternatively, the other external input and output devices 39 may be connected by other interfaces, such as a parallel port, game port or other port. The computing device 20 may further include or be capable of connecting to a flash card memory (not shown) through an appropriate connection port (not shown). The computing device 20 may further include or be capable of connecting with a network through a network port 42 and network interface 43, and through wireless port 46 and corresponding wireless interface 47 may be provided to facilitate communication with other peripheral devices, including other computers, printers, and so on (not shown). The computing device may include other resource(s) 52. It will be appreciated that the various components and connections shown are examples and other components and means of establishing communication links may be used.

The computing device 20 may be primarily designed to include a user interface. The user interface may include a character, a key-based, or another user data input via the touch sensitive display 32. The user interface may include using a stylus (not shown). Moreover, the user interface is not limited to an actual touch-sensitive panel arranged for directly receiving input, but may alternatively or in addition respond to another input device such as the microphone 34. For example, spoken words may be received at the microphone 34 and recognized. Alternatively, the computing device 20 may be designed to include a user interface having a physical keyboard (not shown).

The device functional elements 50 are typically application specific and related to a function of the electronic device, and are coupled with the system bus 23 through an interface (not shown). The functional elements may typically perform a single well-defined task with little or no user configuration or setup, such as a refrigerator keeping food cold, a cell phone connecting with an appropriate tower and transceiving voice or data information, a camera capturing and saving an image, or communicating with an implantable medical apparatus.

In certain instances, one or more elements of the thin computing device 20 may be deemed not necessary and omitted. In other instances, one or more other elements may be deemed necessary and added to the thin computing device.

FIG. 8 and the following discussion are intended to provide a brief, general description of an environment in which embodiments may be implemented. FIG. 8 illustrates an example embodiment of a general-purpose computing system in which embodiments may be implemented, shown as a computing system environment 100. Components of the computing system environment 100 may include, but are not limited to, a general-purpose computing device 110 having a processor 120, a system memory 130, and a system bus 121 that couples various system components including the system memory to the processor 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing system environment 100 typically includes a variety of computer-readable media products.

Computer-readable media may include any nonvolatile media that can be accessed by the computing device 110, and may include removable or non-removable nonvolatile media. By way of example, and not of limitation, computer-readable media may include computer storage media.

Computer storage media includes removable and non-removable nonvolatile media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 110. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media. Computer storage media is a non-transitory computer-readable media.

The system memory 130 includes computer storage media in the form of nonvolatile memory such as ROM 131 and RAM 132. A RAM may include at least one of a DRAM, an EDO DRAM, a SDRAM, a RDRAM, a VRAM, or a DDR DRAM. A basic input/output system (BIOS) 133, containing the basic routines that help to transfer information between elements within the computing device 110, such as during start-up, is typically stored in ROM 131. RAM 132 typically contains data and program modules that are immediately accessible to or presently being operated on by the processor 120. By way of example, and not limitation, FIG. 8 illustrates an operating system 134, application programs 135, other program modules 136, and program data 137. Often, the operating system 134 offers services to applications programs 135 by way of one or more application programming interfaces (APIs) (not shown). Because the operating system 134 incorporates these services, developers of applications programs 135 need not redevelop code to use the services.

The computing device 110 may also include other removable/non-removable, nonvolatile computer readable storage media products. By way of example only, FIG. 8 illustrates a non-removable non-volatile memory interface (hard disk interface) 140 that reads from and writes for example to non-removable, non-volatile magnetic media. FIG. 8 also illustrates a removable non-volatile memory interface 150 that, for example, is coupled to a magnetic disk drive 151 that reads from and writes to a removable, non-volatile magnetic disk 152, or is coupled to an optical disk drive 155 that reads from and writes to a removable, non-volatile optical disk 156, such as a CD ROM. Other removable/non-removable, non-volatile computer storage media that can be used in the example operating environment include, but are not limited to, magnetic tape cassettes, memory cards, flash memory cards, DVDs, digital video tape, solid state RAM, and solid state ROM. The hard disk drive 141 is typically connected to the system bus 121 through a non-removable memory interface, such as the interface 140, and magnetic disk drive 151 and optical disk drive 155 are typically connected to the system bus 121 by a removable non-volatile memory interface, such as interface 150. The computing device may include other resource(s) 125.

The drives and their associated computer storage media discussed above and illustrated in FIG. 8 provide storage of computer-readable instructions, data structures, program modules, and other data for the computing device 110. In FIG. 8, for example, hard disk drive 141 is illustrated as storing an operating system 144, application programs 145, other program modules 146, and program data 147. Note that these components can either be the same as or different from the operating system 134, application programs 135, other program modules 136, and program data 137. The operating system 144, application programs 145, other program modules 146, and program data 147 are given different numbers here to illustrate that, at a minimum, they are different copies.

A user may enter commands and information into the computing device 110 through input devices such as a microphone 163, keyboard 162, and pointing device 161, commonly referred to as a mouse, trackball, or touch pad. Other input devices (not shown) may include at least one of a touch-sensitive screen or display surface, joystick, game pad, satellite dish, and scanner. These and other input devices are often connected to the processor 120 through a user input interface 160 that is coupled to the system bus, but may be connected by other interface and bus structures, such as a parallel port, game port, or a universal serial bus (USB). A display 191, such as a monitor or other type of display device or surface may be connected to the system bus 121 via an interface, such as a video interface 190. A projector display engine 192 that includes a projecting element may be coupled to the system bus. In addition to the display, the computing device 110 may also include other peripheral output devices such as speakers 197 and printer 196, which may be connected through an output peripheral interface 195.

The computing system environment 100 may operate in a networked environment using logical connections to one or more remote computers, such as a remote computer 180. The remote computer 180 may be a personal computer, a server, a router, a network PC, a peer device, or other common network node, and typically includes many or all of the elements described above relative to the computing device 110, although only a memory storage device 181 has been illustrated in FIG. 6. The network logical connections depicted in FIG. 6 include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system environment 100 is connected to the network 171 through a network interface, such as the network interface 170, the modem 172, or the wireless interface 193. The network may include a LAN network environment, or a WAN network environment, such as the Internet. In a networked environment, program modules depicted relative to the computing device 110, or portions thereof, may be stored in a remote memory storage device. By way of example, and not limitation, FIG. 6 illustrates remote application programs 185 as residing on memory storage device 181. It will be appreciated that the network connections shown are examples and other means of establishing a communication link between the computers may be used.

In certain instances, one or more elements of the computing device 110 may be deemed not necessary and omitted. In other instances, one or more other elements may be deemed necessary and added to the computing device.

All references cited herein are hereby incorporated by reference in their entirety or to the extent their subject matter is not otherwise inconsistent herewith.

In some embodiments, "configured" includes at least one of designed, set up, shaped, implemented, constructed, or adapted for at least one of a particular purpose, application, or function.

It will be understood that, in general, terms used herein, and especially in the appended claims, are generally intended as "open" terms. For example, the term "including" should be interpreted as "including but not limited to." For example, the term "having" should be interpreted as "having at least." For example, the term "has" should be interpreted as "having at least." For example, the term "includes" should be interpreted as "includes but is not limited to," etc. It will be further understood that if a specific number of an introduced claim recitation is intended, such an intent will be explicitly recited in the claim, and in the absence of such recitation no such intent is present. For example, as an aid to understanding, the following appended claims may contain usage of introductory phrases such as "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a receiver" should typically be interpreted to mean "at least one receiver"); the same holds true for the use of definite articles used to introduce claim recitations. In addition, even if a specific number of an introduced claim recitation is explicitly recited, it will be recognized that such recitation should typically be interpreted to mean at least the recited number (e.g., the bare recitation of "at least two chambers," or "a plurality of chambers," without other modifiers, typically means at least two chambers).

In those instances where a phrase such as "at least one of A, B, and C," "at least one of A, B, or C," or "an [item] selected from the group consisting of A, B, and C," is used, in general such a construction is intended to be disjunctive (e.g., any of these phrases would include but not be limited to systems that have A alone, B alone, C alone, A and B together, A and C together, B and C together, or A, B, and C together, and may further include more than one of A, B, or C, such as $A_1$, $A_2$, and C together, A, $B_1$, $B_2$, $C_1$, and $C_2$ together, or $B_1$ and $B_2$ together). It will be further understood that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable or physically interacting components or wirelessly interactable or wirelessly interacting components.

With respect to the appended claims the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Use of "Start," "End," "Stop," or the like blocks in the block diagrams is not intended to indicate a limitation on the beginning or end of any operations or functions in the diagram. Such flowcharts or diagrams may be incorporated into other flowcharts or diagrams where additional functions are performed before or after the functions shown in the diagrams of this application. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to one skilled in the art. The various aspects and embodiments disclosed herein are for purposes of illustration and are not intended to be limiting, with the true scope and spirit being indicated by the following claims.

The invention claimed is:

1. A therapeutic oxygen supply apparatus comprising:
   an intake manifold component configured to receive a concentrated oxygen;
   an oxygen-flow control structure component configured to route a flow of the concentrated oxygen between the intake manifold component and a patient manifold component configured to supply the concentrated oxygen to a patient;
   a sensor circuit configured to acquire data indicative of a respective operational state of the intake manifold component;
   a rule-based engine configured to select a next operational state of a component of the intake manifold component and the oxygen-flow control structure component in response to (i) the acquired data indicative of the respective operational state of the intake manifold component and the oxygen-flow control structure component and (ii) a rule database having at least one rule responsive to an objective of providing a therapeutic flow of oxygen to the patient; and
   a configuration manager circuit configured to generate a control signal implementing the selected next operational state in the component of the intake manifold component and the oxygen-flow control structure component.

2. The therapeutic oxygen supply apparatus of claim 1, further including a power supply component configured to supply electrical power to an oxygen concentrator.

3. The therapeutic oxygen supply apparatus of claim 1, wherein the sensor circuit is further configured to acquire data indicative of a quality of the concentrated oxygen in the therapeutic oxygen supply apparatus.

4. The therapeutic oxygen supply apparatus of claim 3, wherein the sensor circuit is further configured to acquire data indicative of the concentrated oxygen present in the intake manifold component.

5. The therapeutic oxygen supply apparatus of claim 1, further including a low oxygen concentration alarm component.

6. The therapeutic oxygen supply apparatus of claim 1, wherein the configuration manager circuit includes an operational-state controller configured to control an operational state of at least one of the intake manifold component and the oxygen-flow control structure component.

7. The therapeutic oxygen supply apparatus of claim 1, wherein the oxygen-flow control structure component is configured to route a flow of the concentrated oxygen from the intake manifold component to a compressor component, an oxygen tank component, and the patient manifold component in response to the control signal.

8. The therapeutic oxygen supply apparatus of claim 1, wherein the oxygen-flow control structure component is configured to route a flow of the concentrated oxygen from the intake manifold component to the patient manifold component in response to the control signal.

9. The therapeutic oxygen supply apparatus of claim 1, further comprising an oxygen concentrator component.

10. The therapeutic oxygen supply apparatus of claim 1, further including a compressor component configured to compress concentrated oxygen received from the oxygen-flow control structure component.

11. The therapeutic oxygen supply apparatus of claim 10, further including an oxygen tank component configured to store concentrated oxygen received from the compressor.

12. The therapeutic oxygen supply apparatus of claim 11, wherein the sensor circuit is further configured to acquire data indicative of the concentrated oxygen present in the oxygen tank component.

13. The therapeutic oxygen supply apparatus of claim 11, wherein the oxygen-flow control structure component is configured in response to the control signal from the configuration manager circuit to route a flow of the concentrated oxygen from the intake manifold to the compressor component, the oxygen tank component, and the patient manifold.

14. The therapeutic oxygen supply apparatus of claim 11, wherein the oxygen-flow control structure component is configured in response to the control signal from the configuration manager circuit to route a flow of the concentrated oxygen from the intake manifold through the oxygen-flow control structure component and to the patient manifold component.

15. The therapeutic oxygen supply apparatus of claim 11, wherein the rule database includes a rule database having (a) at least one first priority rule responsive to an objective of providing a therapeutic flow of oxygen to the patient; and (b) at least one second priority rule responsive to an objective of filling the oxygen tank component.

16. The therapeutic oxygen supply apparatus of claim 1, further including at least one of a compressor component configured to compress concentrated oxygen received from the oxygen-flow control structure component, an oxygen tank component configured to store concentrated oxygen, or the patient manifold component.

* * * * *